United States Patent [19]

Lin et al.

[11] Patent Number: 5,055,628

[45] Date of Patent: Oct. 8, 1991

[54] PREPARATION OF ALPHA-OLEFIN BY ETHENOLYSIS

[75] Inventors: Ronny W. Lin; Marshall B. Nelson; Bruce C. Peters, all of Baton Rouge, La.

[73] Assignee: Ethyl Corporation, Richmond, Va.

[21] Appl. No.: 580,098

[22] Filed: Sep. 11, 1990

[51] Int. Cl.[5] ............................ C07C 6/00; C07C 2/02
[52] U.S. Cl. .................................... 585/ 647; 585/525
[58] Field of Search ................................ 585/647, 525

[56] References Cited

U.S. PATENT DOCUMENTS 3,785,956 12/1971 Banks ..................................... 208/93

OTHER PUBLICATIONS

Xiaoding et al., J. Chem. Soc., Faraday Trans. 1, 1986, 82, pp. 1945-1953.

Primary Examiner—Curtis R. Davis
Attorney, Agent, or Firm—David M. Bunnell

[57] ABSTRACT

Alpha-olefin is prepared from internal and/or vinylidene olefin by reacting the internal and/or vinylidene olefin with ethylene in the presence of a catalyst consisting essentially of $Re_2O_7$ and $B_2O_3$ on $Al_2O_3$.

18 Claims, No Drawings

PREPARATION OF ALPHA-OLEFIN BY ETHENOLYSIS

BACKGROUND

This invention relates generally to the preparation of alpha-olefins from internal or vinylidere olefins and more specifically to a process to ethenolize internal olefins and isomerize/ethenolize vinylidenes to vinyl olefins using a $B_2O_3$ modified $Re_2O_7$ on $Al_2O_3$ catalyst.

The ethylene chain growth process for producing alpha-olefins (vinyl olefins) using triethylaluminum followed by olefin displacement as practiced commercially can produce olefins containing from 4 up to 30 or more carbon atoms. Although mainly alpha-olefins are produced, some vinylidene and internal olefins also result. These olefin by-products are generally less useful than alpha-olefins and in some applications, such as the production of sulfonic acids for detergents, vinylidene olefins form tertiary mercaptans which are very difficult to oxidize to sulfonic acids. Separation of such olefins by distillation is difficult. We have discovered a novel process for upgrading α-olefin mixtures containing such olefins to convert the vinylidene and internal olefins to α-olefins without any significant isomerization of α-olefins.

U.S. Pat. No. 3,785,956 discloses the disproportionation of a feed composed of ethylene and branched and linear olefins with a catalyst such as rhenium oxide on alumina while maintaining the conversion of the linear olefins within the range of about 30–50 percent. It has been reported by Xiaoding et al., J. Chem. Soc. Farady Trans. 1, 1986, 82, 1945-1953 that $Re_2O_7/Al_2O_3$ $B_2O_3-MR_4$ (where M=Sn or Pb and R=alkyl) catalysts can be used for the methathesis of alkenes, especially functionalized alkenes such as methyl oleate. This catalyst system is not useful in the upgrading ethenolysis of alpha-olefin mixtures because of its strong isomerization activity for alpha-olefins.

BRIEF SUMMARY OF THE INVENTION

In accordance with this invention there is provided a process for preparing alpha-olefin from an internal or vinylidene olefin or mixtures thereof comprising reacting said internal or vinylidene olefin or mixtures thereof with ethylene in the presence of a catalyst consisting essentially of $Re_2O_7$ and $B_2O_3$ on $Al_2O_3$.

DETAILED DESCRIPTION

The process of the invention is useful in converting both vinylidene and internal olefins to alpha-olefins either separately or in admixture with one another in any proportions. The process is particularly useful in upgrading alpha-olefin products containing such vinylidene and/or internal olefins and especially those mixtures which result from ethylene chain growth on triethylaluminum followed by olefin displacement. Such olefin products contain from about 4 to 30 or more carbon atoms and usually from about 6 to 30 carbon atoms, depending upon the reaction conditions. When the ethylene chain growth process is used to make olefins containing 12 or less carbon atoms the amount of alpha olefin produced is predominant (80 mole percent or more). When used to make higher olefins the amounts of internal and vinylidene olefins increase such that the mixture can contain, for example, from 0–20 mole percent of internal olefins and from about 5 to 50 mole percent vinylidene olefins and, typically, 1.5 to 8 mole percent internal olefins and 5 to 40 mole percent vinylidene olefins with the balance being alpha-olefins.

The catalyst compositions are prepared, for example, by the impregnation of a high surface area $Al_2O_3$ with an aqueous solution of $Re_2O_7$ (perrhenic acid solution) and $H_3BO_3$. A slight excess of water can be used for good dispersion The impregnated $Al_2O_3$ is then dried in situ or in a tumble dryer and then calcined at a temperature of from about 300° to 650° C., preferably about 450° to 550° C., under dry air or oxygen for 0.5 to 10 hours. Particularly effective catalyst compositions contain from about 4 to 20 weight percent $Re_2O_7$ and from about 0.5 to 6 weight percent $B_2O_3$ on $Al_2O_3$ and especially 10–15 weight percent $Re_2O_7$ and 0.5 to 2 weight percent $B_2O_3$ on $Al_2O_3$.

The catalyst is used in an amount which is effective to ethenolize internal olefins and isomerize/ethenolize vinylidene olefins to vinyl olefins at a reasonable rate. Weight ratios of from about 10 to 100 olefin to catalyst are suitable and preferably about 30 to 60 (1 to 10 wt % catalyst and, preferably, 1.5 to 3.5 wt % catalyst based on the total weight of olefins in the reaction mixture). The catalyst can be regenerated by heat-treatment to remove residual olefins and burning off the residual coke at about 400° to 525° C. with $N_2$ and then diluted air ($N_2$) prior to calcination.

It is believed that the catalyst first promotes the isomerization of the vinylidene olefin to a trisubstituted olefin which can then be ethenolized to provide an alpha-olefin and a new vinylidene olefin of lower molecular weight. The latter vinylidene olefin can then be more easily removed from the α-olefins by conventional techniques such as distillation.

The reaction is carried out, for example, in a pressure vessel with agitation under an ethylene pressure of about 300 to 3000 psig and preferably from about 700 to 1500 psig at temperature of from about 25° to 100° C. and preferably from about 40° to 85° C.

The invention is further illustrated by, but is not intended to be limited to, the following examples.

CATALYST PREPARATION

A $Re_2O_7/B_2O_3/Al_2O_3$ catalyst is prepared which contains 10 wt % $Re_2O_7$ and 1.9 wt % $B_2O_3$ on $Al_2O_3$ by the following procedure.

1. Dissolve 0.30 gram $H_3BO_3$ in 9.0 grams of 10 wt % $Re_2O_7$ in water solution (a perrhenic acid solution) with or without warm-up.
2. Add 9.0 grams of high surface area (HSA) $Al_2O_3$ support to absorb the solution.
3. Calcine the catalyst under dry air (usually 2 SCFH) at high temperature (usually 500°–525° C.) for 1–5 hours (usually 2 hours).
4. Cool down the calcined $Re_2O_7$ (10 wt %)/$B_2O_3$ (1.9 wt %)/$Al_2O_3$ catalyst with air or $N_2$, and store in a glass bottle free from moisture.

Catalysts with different amounts of $Re_2O_7$ and $B_2O_3$ are prepared by varying the amounts of $H_3BO_3$ and $Re_2O_7$ which are added to the $Al_2O_3$ support.

EXAMPLE 1

Under a small $N_2$ purge, a clean, dry, 300 cc stainless steel autoclave is charged with 3.0 grams of calcined $Re_2O_7$ (4.8 wt %)/$B_2O_3$ (5.6 wt %)/$Al_2O_3$ catalyst and grams of a dry, primarily $C_{16-20}$ olefin mixture. The autoclave is closed, pressure tested with about 200 psig ethylene and then charged with 770 psig ethylene. The autoclave is heated to 50° C. with agitation and maintained at about 50° C. with the ethylene pressure ranging from 830–970 psig. Samples are taken through a dip tube and analyzed by gas chromatograph and NMR. After reaction the autoclave is cooled and excess ethylene vented. The olefin solution is decanted and the catalyst saved for regeneration. The reaction data is set out in Table I along with a comparison run in which the catalyst did not contain any $B_2O_3$.

and vinylidene olefins to α-olefins that the comparison using only a $Re_2O_7/Al_2O_3$ catalyst

EXAMPLES 2–3

The process of Example 1 is repeated using 86 and 123.8 grams of a dry primarily α-$C_{14}$ olefin mixture and 2.87 and 2.07 grams of catalysts containing 5 and 10 wt percent $Re_2O_7$ and 3.8 wt % $B_2O_3$ on $Al_2O_3$, respectively. The reaction data is set out in Table II along with a comparison in which the catalyst contained no $B_2O_3$.

TABLE I

| Ex. No. | Wt % on $Al_2O_3$ $Re_2O_7$ | $B_2O_3$ | Wt. % Cat. Used On Olefins | Ethylene psig | RXN Temp. °C. | RXN Time Hr. | GC Area % $C^=_{\leq 15}$ | $C^=_{16-18-20}$ | $C^=_{17-19-21}{}^+$ |
|---|---|---|---|---|---|---|---|---|---|
| Feed[2] | | | | | | | 1.5 | 97.74 | 0.19 |
| Ex.1 | 4.8 | 5.6 | 6.0 | 830–970 | 50 | | | | |
| A | | | | | | 1.5 | 49.45 | 33.46 | 15.07 |
| B | | | | | | 3.0 | 59.09 | 24.26 | 14.51 |
| C | | | | | | 4.5 | 62.19 | 19.60 | 16.16 |
| Compar | 4.8 | 0.0 | 6.0 | 920–970 | 50 | | | | |
| A | | | | | | 1.5 | 16.67 | 76.01 | 6.32 |
| B | | | | | | 3.0 | 21.92 | 66.65 | 10.47 |
| C | | | | | | 4.5 | 24.84 | 64.39 | 9.74 |

| Ex. No. | ~% Conv. of $C^=_{16-18-20}$ | NMR[1] α | Vd. | Tri. | Int. |
|---|---|---|---|---|---|
| Feed[2] | | 1.9 | 15.0 | 6.3 | 76.8 |
| Ex. 1 | | | | | |
| A | 66.5 | 54.2 | 0.7 | 14.8 | 30.3 |
| B | 75.7 | 68.8 | 0.8 | 6.6 | 23.8 |
| C | 80.4 | 69.0 | 0.6 | 10.0 | 20.4 |
| Compar | | | | | |
| A | 24.0 | 21.7 | 10.1 | 8.0 | 60.2 |
| B | 33.4 | 29.8 | 9.0 | 5.6 | 55.6 |
| C | 35.6 | 33.4 | 8.6 | 5.8 | 52.2 |

[1] α = alpha olefins; Vd. = vinylidenes; Tri. = trisubstituted olefins; Int. = internal olefins.
[2] Isomerized $C^=_{16-18-20}$ olefins for studies.

The NMR results demonstrate that the process of Example 1 converted significantly more of the internal a comparison in which the catalyst contained no $B_2O_3$.

TABLE II

| Ex. No. | Wt % on $Al_2O_3$ $Re_2O_7$ | $B_2O_3$ | Wt. Ratio of Olefins to Cat. | $C_2H_4$ psig | RXN Temp. °C. | RXN Time Hr. | Analytical GC Area % $C^=_{\leq 13}$ | $C^=_{14}$ α | Int. | Others[3] | $C^=_{\geq 15}$ |
|---|---|---|---|---|---|---|---|---|---|---|---|
| Feed | | | | | | | 0.11 | 83.69 | 3.90 | 11.14 | 1.08 |
| Compar | 10.0 | 0.0 | 30.0 | 945 | 50 | | | | | | |
| A | | | | | | 5.0 | 4.92 | 80.59 | 0.64 | 8.52 | 5.34 |
| B | | | | | | 22.3 | 7.28 | 79.77 | 0.08 | 6.42 | 6.46 |
| C | | | | | | 25.0 | 7.51 | 79.59 | 0.07 | 6.26 | 6.58 |
| Ex. 2 | 5.0 | 3.8 | 30.0 | 970 | 50 | | | | | | |
| A | | | | | | 2.5 | 5.12 | 81.01 | 1.50 | 7.08 | 5.31 |
| B | | | | | | 7.0 | 7.54 | 80.04 | 0.69 | 4.99 | 6.79 |
| C | | | | | | 19.0 | 9.73 | 78.24 | 0.29 | 3.52 | 8.17 |
| D | | | | | | 21.0 | 9.86 | 78.36 | 0.27 | 3.33 | 8.18 |
| Ex. 3 | 10.0 | 3.8 | 59.8 | 960 | 50 | | | | | | |
| A | | | | | | 2.0 | 2.5 | 83.09 | 2.59 | 8.69 | 3.15 |
| B | | | | | | 18.0 | 7.1 | 81.06 | 0.98 | 5.48 | 5.39 |
| C | | | | | | 25.0 | 8.09 | 79.77 | 0.80 | 5.34 | 6.00 |

| Ex. No. | GC % in Total Olefins[4] $C^=_{14's}$ | α-$C^=_{14}$ + $C^=_{26}$ | % of α-$C^=_{14}$ in $C^=_{14's}$ | Relative Activity of Cat. |
|---|---|---|---|---|
| Feed | 98.73 | 83.69 | 84.8 | |
| Compar | | | | 100 |
| A | 89.75 | 83.46 | 89.8 | |
| B | 86.27 | 83.57 | 92.5 | |
| C | 85.92 | 83.46 | 92.6 | |
| Ex. 2 | | | | 100+ |
| A | 89.59 | 83.39 | 90.4 | |
| B | 85.72 | 83.36 | 93.4 | |
| C | 82.10 | 82.40 | 95.4 | |
| D | 81.96 | 82.48 | 95.6 | |
| Ex. 3 | | | | 200 |
| A | 94.37 | 84.34 | 88.0 | |
| B | 87.52 | 83.63 | 92.6 | |

TABLE II-continued

|   | C | 85.91 | 82.59 | 92.9 |
|---|---|-------|-------|------|

[3] Mainly vinylidene.
[4] $\alpha$-$C_{14}^=$ (alpha $C_{14}^=$) % in $C^{14=}$'s is a measure of selective performance of the catalyst. Percentage of $\alpha$-$C_{14}^=$ plus $C_{26}^=$ is a measure of isomerization of $\alpha$-olefin(s) by the catalyst.

$\alpha$-$C_{14}^=$ (alpha $C_{14}^=$) % in $C^{14=}$'s is a measure of selective performance of the catalyst. Percentage of $\alpha$-$C_{14}^=$ plus $C_{26}^=$ is a measure of isomerization of $\alpha$-olefin(s) by the catalyst.

The results show that the $Re_2O_7/B_2O_3/Al_2O_3$ catalysts of Examples 2 and 3 gave equivalent results to the $Re_2O_7/Al_2O_3$ comparison using, in the case of Example 2 a catalyst having one-half the amount of $Re_2O_7$, and in the case of Example 3, a catalyst having the same amount of $Re_2O_7$ but at only one-half the catalyst concentration.

The regenerated catalyst was used to enthenolize additional $\alpha$-$C_{14}$ olefin mixture. The reaction data is set out in Table III.

TABLE III

| Ex. No. | Wt % on $Al_2O_3$ $R_2O_7$ | $B_2O_3$ | Wt. Ratio of Olefins to Cat. | $C_2H_4$ psig | RXN Temp. °C. | RXN Time Hr. | GC (Analytical) Area % |  |  |  |  |
|---------|---|---|---|---|---|---|---|---|---|---|---|
|  |  |  |  |  |  |  | $C^=_{7-12}$ | $C^=_{13}$ | 1-$C^=_{14}$ | I-$C^=_{14}$ | Other $C^=_{14}$ |
| 4 | 10 | 1.9 | 16.0 | 850 | 50 |  |  |  |  |  |  |
| A |  |  |  |  |  | 2 | 3.88 | 3.48 | 79.06 | 0.51 | 5.80 |
| B |  |  |  |  |  | 4 | 5.25 | 4.13 | 78.31 | 0.18 | 3.88 |
| 4[1] | 10 | 1.9 | 16.0 | 870 | 50 |  |  |  |  |  |  |
| A |  |  |  |  |  | 2 | 3.75 | 3.26 | 80.65 | 0.44 | 4.34 |
| B |  |  |  |  |  | 4 | 5.80 | 4.05 | 78.57 | 0.15 | 3.38 |

| Ex. No. | GC (Analytical) Area % | | % of $C^=_{14}$'s | 1-$C^=_{14}$ in $C^=_{14}$'s | 1-$C^=_{14}$ Plus $C^=_{26}$ |
|---|---|---|---|---|---|
|  | $C^=_{15-25}$ | $C^=_{26}$ |  |  |  |
| 4 |  |  |  |  |  |
| A | 3.29 | 3.98 | 85.37 | 92.6 | 83.04 |
| B | 3.60 | 4.65 | 82.37 | 95.1 | 82.96 |
| 4[1] |  |  |  |  |  |
| A | 3.68 | 4.35 | 85.43 | 94.4 | 85.00 |
| B | 3.45 | 4.62 | 82.10 | 95.7 | 83.19 |

[1] Regenerated catalyst

EXAMPLE 4

A $\alpha$-$C_{14}$ olefin mixture similar to that used in Example 2 is upgraded by ethenolysis according to the following procedure.

Under a small $N_2$ purge, charge a clean, dry 300 cc S.S. autoclave with 3.75 grams of calcined $Re_2O_7$ (10 wt %)/$B_2O_3$ (1.9 wt %)/$Al_2O_3$ catalyst Add 60.0 grams dry 1-$C_{14}^=$ olefin (about 85% $\alpha$-olefin, 10% vinylidenes and 5% internal olefins). Then close up the autoclave. After pressure test with 200 psig ethylene, charge the reactor with 700-800 psig ethylene. Heat up to 50° C. with agitation on. Run the reaction at about 50° C. under about 850 psig.

Take samples during the reaction through a ⅛" dip-tube.

After the reaction, cool down and vent off excess ethylene. Decant the metathetic olefin solution and save the catalyst for regeneration.

Regeneration of the Spent Catalyst
1. Heat up the spent catalyst under $N_2$ (~2 SCFH) purge to 400°-500° C. to remove residual olefin.
2. Slowly introduce air to $N_2$ to burn off coke on the catalyst at 480°-525° C. (The black coke is formed during the heat treatment for removal of residual olefins.)
3. Calcine the catalyst as described above under Catalyst Preparation.

The results demonstrate that the regenerated catalyst is still effective.

EXAMPLE 5

The process of Example 4 is repeated except that the catalyst contains 0.5 wt % $B_2O_3$. The results show a catalyst efficiency of 115+ compared with 100 for the same olefin to catalyst ratio using a $Re_2O_7/Al_2O_3$ catalyst.

The foregoing examples illustrate carrying out of the process of the invention in a batch mode. It should be understood that the process can also be carried out in a continuous mode by passing the olefin feed and ethylene through a fixed bed of the $Re_2O_7/B_2O_3/Al_2O_3$ catalyst.

What is claimed is:

1. A process for preparing alpha-olefin from an internal or vinylidene olefin or mixtures thereof comprising reacting said internal or vinylidene olefin or mixtures thereof with ethylene in the presence of a catalyst consisting 5 essentially of $Re_2O_7$ and $B_2O_3$ on $Al_2O_3$.

2. The process of claim 1 wherein the catalyst contains from about 0.4 to 6 weight percent $B_2O_3$ and from about 5 to 20 wt percent $Re_2O_7$.

3. The process of claim 1 wherein the catalyst is present in an amount of from about 1 to 10 weight percent based on the total weight of olefins in the reaction mixture.

4. The process of claim 1 wherein the olefin is an internal olefin.

5. The process of claim 1 wherein the olefin is a vinylidene olefin.

6. The process of claim 1 wherein the process is carried out under an ethylene pressure of from about 300 to 3000 at a reaction temperature of from about 25° to 100° C.

7. The process of claim 5 wherein the ethylene pressure is from about 700 to 1500 psig and the temperature is from about 40° to 85° C.

8. The process of claim 1 wherein the olefin is a mixture of internal and vinylidene olefins.

9. A process for upgrading an alpha-olefin mixture which contains internal and/or vinylidene olefins so as to convert at least a portion of said olefins to alpha-olefin comprising reacting said mixture with ethylene in the presence of a catalyst consisting essentially of $Re_2O_7$ and $B_2O_3$ on $Al_2O_3$.

10. A process according to claim 9 wherein said mixture contains from about 0–20 mole percent internal olefin from about 5 to 40 mole percent vinylidene olefin with the balance being alpha-olefin.

11. The process of claim 9 wherein the catalyst contains from about 0.4 to 6 weight percent $B_2O_3$ and from about 5 to 20 wt percent $Re_2O_7$.

12. The process of claim 9 wherein the catalyst is present in an amount of from about 1 to 10 weight percent based on the total weight of olefins in the reaction mixture.

13. The process of claim 10 wherein the catalyst contains from about 0.4 to 6 weight percent $B_2O_3$ and from about 5 to 20 wt percent $Re_2O_7$.

14. The process of claim 10 wherein the catalyst is present in an amount of from about 1 to 10 weight percent based on the total weight of olefins in the reaction mixture.

15. The process of claim 9 wherein the process is carried out under an ethylene pressure of from about 300 to 3000 psig at a reaction temperature of from about 25° to 100.C.

16. The process of claim 15 wherein the ethylene pressure is from about 700 to 1500 psig and the temperature is from about 40° to 85° C.

17. The process of claim 10 wherein the process is carried out under an ethylene pressure of from about 300 to 3000 psig at a reaction temperature of from about 25° to 100° C.

18. The process of claim 17 wherein the process is carried out under an ethylene pressure of from about 700 to 1500 psig at a reaction temperature of from about 40° to 85° C.

* * * * *

UNITED STATES PATENT AND TRADEMARK OFFICE
CERTIFICATE OF CORRECTION

PATENT NO. : 5,055,628

DATED : October 8, 1991

INVENTOR(S) : RONNY W. LIN, ET AL.

It is certified that error appears in the above-identified patent and that said Letters Patent is hereby corrected as shown below:

In the Claims:

Column 6, line 53, reads: -- sisting 5 essentially -- but should read: "sisting essentially"

Column 6, line 67, reads: -- 3000 at a reaction -- but should read: "3000 psig at a reaction"

Column 8, line 11, reads: -- $25°$ to 100.C. -- but should read: "$25°$ to $100°C$."

Signed and Sealed this

Second Day of March, 1993

Attest:

STEPHEN G. KUNIN

Attesting Officer

Acting Commissioner of Patents and Trademarks